United States Patent [19]

Schulten et al.

[11] 4,117,102

[45] Sep. 26, 1978

[54] THERMOCHEMICAL PROCESS FOR PRODUCING METHANE AND OXYGEN FROM CARBON OXIDES AND WATER

[75] Inventors: Rudolf Schulten, Richterich; Friedrich Behr, Gross Denkte, both of Germany

[73] Assignee: Rheinische Braunkohlenwerke AG, Cologne, Germany

[21] Appl. No.: 791,720

[22] Filed: Apr. 28, 1977

[30] Foreign Application Priority Data

Apr. 30, 1976 [DE] Fed. Rep. of Germany ....... 2619399

[51] Int. Cl.$^2$ .............................................. C01B 13/00
[52] U.S. Cl. ................................. 423/579; 260/676 R
[58] Field of Search ............... 423/500, 539, 481, 579; 260/676 R

[56] References Cited

U.S. PATENT DOCUMENTS

| | | | |
|---|---|---|---|
| 2,143,222 | 1/1939 | Heath | 423/481 X |
| 3,888,750 | 6/1975 | Brecher et al. | 423/539 X |
| 3,929,980 | 12/1975 | Abraham et al. | 423/500 X |
| 3,995,016 | 11/1976 | Kittle | 423/500 X |
| 4,056,607 | 11/1977 | Behr | 423/579 |

FOREIGN PATENT DOCUMENTS 48-995  1/1973  Japan ........................................ 423/500

OTHER PUBLICATIONS

J. W. Mellor's "A Comp. Treatise on Inorg. and Theo. Chem.", vol. 5, 1924 Ed., p. 938, Longmans, Green & Co., N.Y.

Primary Examiner—O. R. Vertiz
Assistant Examiner—Wayne A. Langel
Attorney, Agent, or Firm—Burns, Doane, Swecker & Mathis

[57] ABSTRACT

The invention comprises a recirculatory process for producing hydrocarbons and oxygen in which sulphur dioxide is reacted with iodine and water to form a hydrogen polyiode or a hydrate thereof and sulphuric acid, the sulphuric acid is separated and thermally decomposed to form water sulphur dioxide and oxygen, the polyiodide or its hydrate is decomposed to form iodine and gaseous hydrogen iodide which is concurrently or separately reacted with a carbon oxide or mixture of carbon oxides to form hydrocarbons especially methane and water, the hydrocarbons and water being removed from the system and the remaining reaction products recirculated.

12 Claims, 1 Drawing Figure

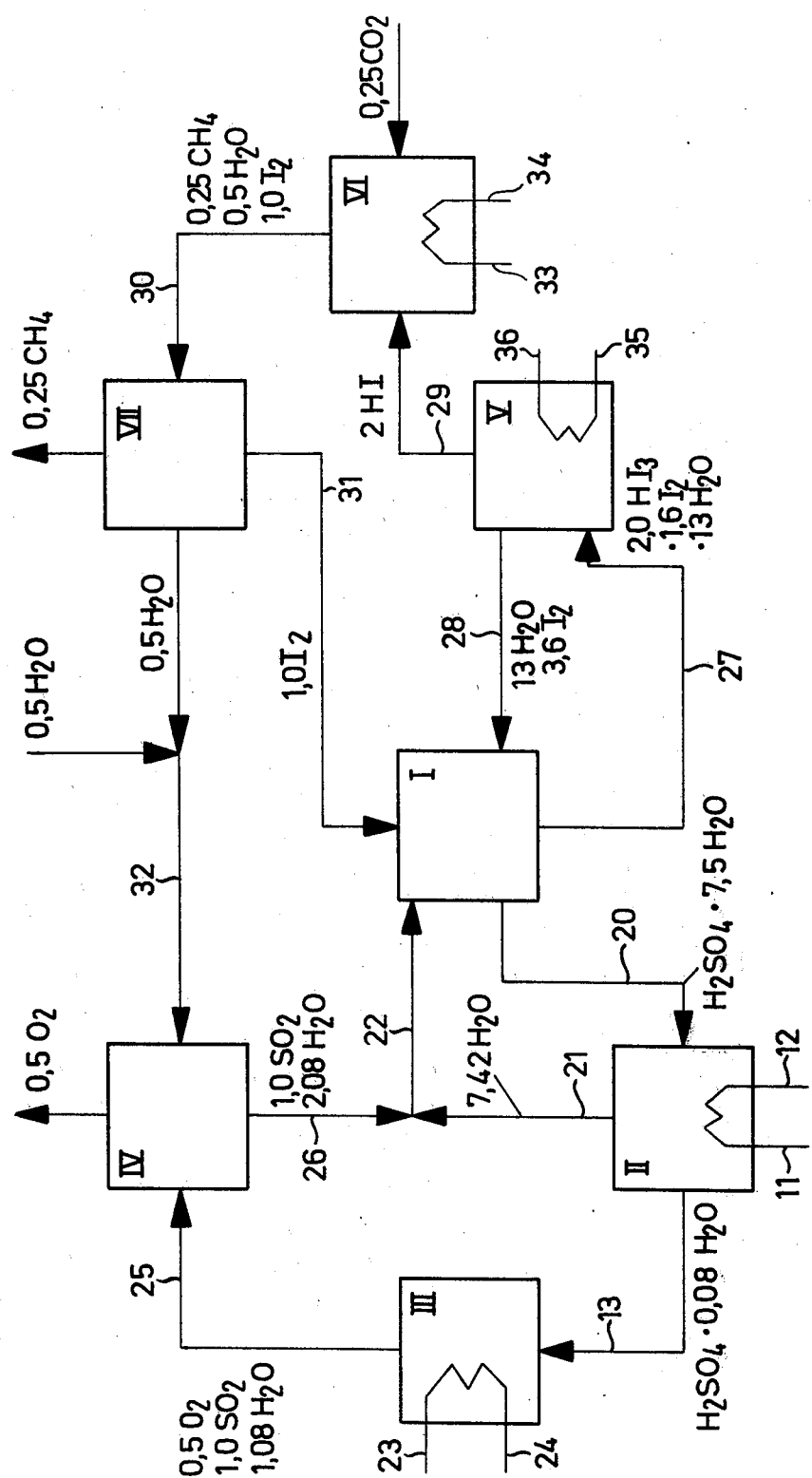

THERMOCHEMICAL PROCESS FOR PRODUCING METHANE AND OXYGEN FROM CARBON OXIDES AND WATER

The invention relates to a process in which carbon monoxide and/or carbon dioxide is reduced to hydrocarbons by using chemical components carried in recirculatory systems, and heat and oxygen at the same time being released. The heat required for this purpose can originate from a nuclear reactor.

Work hitherto carried out in the use of nuclear heat has been particularly directed towards the thermochemical decomposition of water into hydrogen and oxygen. It is possible to use the hydrogen, thus obtained, for the purpose of reducing carbon oxides to methane. However, this means that a separate exothermic processing step is required in addition to the thermochemical decomposition of the water, so that this method is more expensive than reductions which are effected directly by using a component which can be used in a recirculatory system.

The object of the invention is, inter alia, to develop a process of the type described in which the number of steps or stages of the process is minimized and the quantity of heat to be exchanged is kept as small as possible. In particular, carbon dioxide or carbon monoxide is to be reduced by a process which does not include interposing a water-decomposition plant, i.e. a component, giving off hydrogen, is carried in a recirculatory system and, together with a carbon oxide, forms methane. Furthermore, the use of carbon dioxide is desirable, since this constitutes the simplest form of recycling carbon.

This object is achieved in accordance with the invention by a recirculatory process in which water and sulphur dioxide is reacted, in an exothermic reaction, with iodine and water to form sulphuric acid and hydrogen polyiodide, e.g., hydrogen triiodide or the hydrate thereof; the sulphuric acid which is produced is separated from the reaction mixture, thermally concentrated and decomposed at increased temperatures, optionally in the presence of catalysts ($V_2O_5$), to release oxygen; the hydrogen polyiodide produced, or its hydrate, is decomposed to release iodine and form gaseous hydrogen iodide which is concurrently, or in a separate reaction stage, reacted with carbon monoxide and/or carbon dioxide; the hydrocarbons and the oxygen so obtained are removed from the process and the other components are reintroduced at the appropriate stages of the recirculatory process.

Advantageously, the formation of hydrogen polyiodide and sulphuric acid from iodine and sulphur dioxide in the presence of water is effected at temperatures of approximately 20° to 60° C. The concentration of the resulting sulphuric acid is maintained at approximately 60 to 90%. The products obtained can be separated from one another as two liquid phases. Alternatively, hydrogen iodide formed during the course of the reaction can be bound in a complex with, for example, $CI_2$, and then separated from the sulphuric acid. The decomposition of the sulphuric acid into water, sulphur dioxide and oxygen can be effected (in a known manner,) and also the separation of the said compounds. In accordance with the invention, the heat produced during reaction of hydrogen iodide with a carbon oxide can be used in the recirculatory process for, for example, preheating the materials used, or alternatively, for releasing gaseous hydrogen iodide from the hydrated iodine complex.

In accordance with the invention, the carbon dioxide is reduced in accordance with the equations:

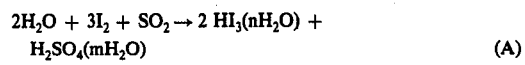

$$2H_2O + 3I_2 + SO_2 \rightarrow 2\ HI_3(nH_2O) + H_2SO_4(mH_2O) \quad (A)$$

$$H_2SO_4 \rightarrow H_2O + SO_2 + \tfrac{1}{2} O_2 \quad (B)$$

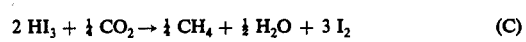

$$2\ HI_3 + \tfrac{1}{4} CO_2 \rightarrow \tfrac{1}{4} CH_4 + \tfrac{1}{2} H_2O + 3\ I_2 \quad (C)$$

When using carbon monoxide, the circulatory process takes place in accordance with the following equations:

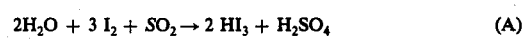

$$2H_2O + 3\ I_2 + SO_2 \rightarrow 2\ HI_3 + H_2SO_4 \quad (A)$$

$$H_2SO_4 \rightarrow H_2O\ SO_2 + \tfrac{1}{2} O_2 \quad (B)$$

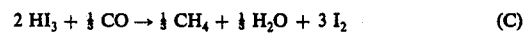

$$2\ HI_3 + \tfrac{1}{4} CO \rightarrow \tfrac{1}{4} CH_4 + \tfrac{1}{4} H_2O + 3\ I_2 \quad (C)$$

In both cases, a catalyst from the eighth intermediate group of the periodic system of the elements, or bismuth (III)-iodide, can be used in the temperature range of from approximately 200°–500° C during reduction.

Carbon monoxide can be obtained, in accordance with the following equation, in a conventional manner by means of a reformer, from methane produced and carbon dioxide extracted from, for example, the flue gas of a coal-fired power plant, with the formation of steam $$3\ CO_2 + CH_4 \rightarrow 4\ CO + 2H_2O \quad (600° - 850°\ C)$$

Furthermore, it is also possible to produce higher hydrocarbons instead of methane, by means of special catalysts if required. Methane thereby produced as a by-product can in turn be converted to carbon monoxide by means of a reformer and reintroduced into the process:

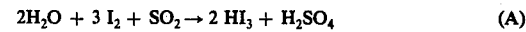

$$2H_2O + 3\ I_2 + SO_2 \rightarrow 2\ HI_3 + H_2SO_4 \quad (A)$$

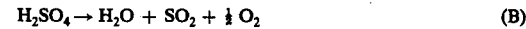

$$H_2SO_4 \rightarrow H_2O + SO_2 + \tfrac{1}{2} O_2 \quad (B)$$

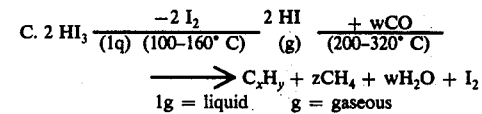

$$C.\ 2\ HI_3 \xrightarrow[\text{(lq)}]{-2\ I_2} \underset{\text{(g)}}{2\ HI} \xrightarrow[\text{(200-320° C)}]{+ wCO} \ C_xH_y + zCH_4 + wH_2O + I_2$$

lq = liquid    g = gaseous

A hydrocarbon mixture $C_xH_y + zCH_4$ is obtained as a product and also contains methane. The other two components $wH_2O + I_2$ are reintroduced into the circuit.

The advantages of the process in accordance with the invention become apparent, particularly in comparison with direct decomposition of hydrogen iodide to form hydrogen and iodine, when it is taken into account that, despite the use of high temperatures (450° to 700° C), only a small portion (20 to 35%) of the hydrogen iodide decomposes, so that it is necessary to recycle the gas mixture several times and there is a considerable expenditure on heat and separating operations. By virtue of the reduction process in accordance with the invention (reaction of carbon in each case), the equilibrium is displaced to the right in an advantageous manner, that is in the direction towards the products to be obtained.

One embodiment of the invention is shown diagrammatically in the drawing in the form of a flow chart. The mass balance is given in molar numbers per 0.5 mol $O_2$. Only those substances are taken into account which effectively participate in the reactions. Non-reacted substances are reintroduced into the particular processing stage. They are not taken into account in the flow chart and in the mass balance.

1.0 of $SO_2$ and a total of 9.5 of $H_2O$ (1q) is fed to the reactor I by way of the pipe 22, 1.0 of $I_2$(1q) is fed to the reactor I by way of the pipe 31, and 13 of $H_2O$ (1q) and 3.6 of $I_2$(1q) are fed to the reactor I by way of the pipe 28. At a temperature of approximately 20°–60° C and a pressure of 2.7 atm, $SO_2$ is reacted in an exothermic reaction in the reactor I with $I_2$ and $H_2O$ to form 1.0 of $H_2SO_4$. 7.5 of $H_2O$ (1q) + 2 [$HJ_3$. 0.8 of $I_2$. 6.5 of $H_2O$] (1q). The sulphuric acid is separated from the resultant mixture and fed by way of a pipe 20 to the apparatus II where it is thermally concentrated. The medium required for heating is fed and discharged in the form of steam by way of pipes 11 and 12. The sulphuric acid is concentrated in the apparatus II at temperatures up to 335° C and at a pressure of 1.0 atm.

The 7.42 of $H_2O$ separated from the sulphuric acid in the apparatus II are reintroduced into the reactor I by way of pipes 21 and 22. 1.0 of $H_2SO_4$. 0.08 of $H_2O$ are fed by way of a pipe 13 to a reactor III in which they are vaporized in the presence of $V_2O_5$ catalysts with the release of oxygen. This occurs at temperatures of from 335° to 950° C and at a pressure between 1 and 10 atm. The medium required for heating is fed by way of a pipe 23 and is discharged by way of a pipe 24.

The resultant 1.08 of $H_2O$ + 1.0 of $SO_2$ + 0.5 of $O_2$ is fed through a pipe 25 to a separating apparatus IV in which 0.5 of $O_2$ is separated and conducted out of the system. As already mentioned, 1.0 of $SO_2$ + 2.08 of $H_2O$ enter the reactor I by way of pipes 26 and 22.

In addition to the $H_2SO_4$. 7.5 $H_2O$ discharged by way of the pipe 20, 2 [$HI_3$. 0.8 $I_2$. 6.5 $H_2O$] (1q) has also been produced in the reactor I and is fed through a pipe 27 to a reactor V in which the hydrogen iodide is released, 13.0 $H_2O$ (1q) + 3.6 $I_2$(1q) + 2HI (g) being produced. The medium required to heat the reactor is fed by way of a pipe 35 and is discharged by way of a pipe 36. 3.6 $I_2$ + 13 $H_2O$ are reintroduced into the reactor I by way of a pipe 28.

2 HI flow through a pipe 29 into the reactor VI in which the hydrogen iodide is catalytically reacted with carbon dioxide, fed from the outside, in accordance with the equation 0.25 $CO_2$ + 2 HI → 0.25 $CH_4$ + 0.5 $H_2O$ + $I_2$. This reaction is effected at temperatures between 200° and 500° C and a pressure between 10 and 60 atm. The required heat medium is fed and discharged by way of the respective pipes 33 and 34.

The resultant mixture of 0.25 $CH_4$ + 0.5 $H_2O$ + 1.0 $I_2$ flows through a pipe 30 into the separating apparatus VII in which the methane (0.25 $CH_4$) produced in the reactor VI is separated and removed from the circuit. The remaining 1.0 $I_2$ is returned directly to the reactor I through a pipe 31. The remaining water (0.5 $H_2O$) is fed to the separating apparatus IV by way of a pipe 32 into which 0.5 $H_2O$ is additionally fed from the outside, and then to the reactor I together with the 1.0 $SO_2$ carried in the circuit.

We claim:

1. A recirculatory process for producing methane and oxygen which comprises:
   (a) reacting sulphur dioxide with iodine and water in an exothermic reaction to form sulphuric acid and a polyiodide comprising a member selected from the group consisting of hydrogen triiodide and hydrogen triiodide hydrate,
   (b) separating the resulting sulphuric acid from the reaction mixture formed in step (a),
   (c) thermally concentrating and disposing the sulphuric acid separated in step (b) at increased temperature to form water, sulphur dioxide and oxygen,
   (d) decomposing the polyiodide formed in step (a) to form iodine and gaseous hydrogen iodide,
   (e) reacting the so formed gaseous hydrogen iodide with a carbon oxide selected from carbon monoxide, carbon dioxide and a mixture of carbon monoxide and carbon dioxide at an elevated temperature from 200° to 500° C. and at a pressure from 10 to 60 atmospheres to form methane and water, ps and in which the methane formed in step (e) and oxygen formed in step (c) are removed from the system and the remaining products of reaction formed in steps (a), (c), (d) and (e) are re-utilised in steps (a) to (e).

2. A process as claimed in claim 1 in which a reservoir of sulphuric acid formed by reaction (a) is maintained, and the concentration of sulphuric acid in that reservoir is from 60% through 90%.

3. A process as claimed in claim 1 in which the carbon oxide is carbon dioxide.

4. A process as claimed in claim 1 in which the decomposition of the polyiodide and reaction of the gaseous hydrogen iodide are conducted concurrently.

5. A process as claimed in claim 1 in which reaction (a) is conducted at a temperature of 20° C through 60° C.

6. A process as claimed in claim 1 in which reaction (c) is effected in the presence of a catalyst for the reaction.

7. A process as claimed in claim 4 in which the catalyst is vanadium pentoxide.

8. A process as claimed in claim 1 in which reaction (e) is conducted in the presence of a catalyst for the reaction.

9. A process as claimed in claim 6 in which the catalyst is selected from the group consisting of the elements of the eighth intermediate group of the Periodic Table and bismuth (III)-iodide.

10. A recirculatory process for producing methane and oxygen which comprises:
   (a) reacting sulphur dioxide with iodine and water at a temperature of from 20° C. through 60° C. to form sulphuric acid and a polyiodide comprising a member selected from the group consisting of hydrogen triiodide and hydrogen triiodide hydrate,
   (b) separating the resulting sulphuric acid from the reaction mixture formed in step (a),
   (c) thermally concentrating and decomposing the sulphuric acid separated in step (b) at increased temperature to form water, sulphur dioxide and oxygen,
   (d) decomposing the polyiodide formed in step (a) to form iodine and gaseous hydrogen iodide and
   (e) concurrently reacting the gaseous hydrogen iodide with a carbon oxide selected from carbon monoxide, carbon dioxide and a mixture of carbon monoxide and carbon dioxide at a temperature of from 200° C. through 500° C. and at a pressure from 10 to 60 atmospheres in the presence of a catalyst selected from the group consisting of the elements of the eighth intermediate group of the Periodic Table and bismuth (III)-iodide to form methane and water, and removing the methane and oxygen formed respectively in steps (e) and (c) from the system and re-utilising the remaining reaction products in steps (a) to (e).

11. A process as claimed in claim 10 in which the carbon oxide is carbon dioxide.

12. A process as claimed in claim 10 in which a reservoir of sulphuric acid produced in reaction (a) is formed and maintained at a concentration of from 60% through 90%.

* * * * *